United States Patent [19]

Friemel et al.

[11] Patent Number: 4,812,291
[45] Date of Patent: Mar. 14, 1989

[54] METHOD OF FUMIGATING AGRICULTURAL PRODUCTS USING HYDROGEN PHOSPHIDE

[75] Inventors: Wolfgang Friemel, Heppenheim; Volker Barth, Ludwigshafen; Martin Münzel, Bensheim; Reiner Ehret, Weinheim, all of Fed. Rep. of Germany

[73] Assignee: Detia Freyberg GmbH, Laudenbach, Fed. Rep. of Germany

[21] Appl. No.: 25,038

[22] Filed: Mar. 12, 1987

[30] Foreign Application Priority Data

Mar. 12, 1986 [DE] Fed. Rep. of Germany ....... 3608256

[51] Int. Cl.⁴ ................................................. A23L 3/34
[52] U.S. Cl. ........................................ 422/28; 422/30; 422/32; 43/125; 426/320; 426/419
[58] Field of Search ..................................... 422/28–30, 422/32; 423/210; 43/124, 125; 55/73; 426/312, 320, 419

[56] References Cited

U.S. PATENT DOCUMENTS

| | | | |
|---|---|---|---|
| 1,108,521 | 8/1914 | Scheuermann | 422/29 X |
| 1,150,119 | 8/1915 | Hosking | 426/419 X |
| 1,401,292 | 12/1921 | Van Meter | 43/125 |
| 3,097,916 | 7/1963 | Dawson et al. | 422/32 X |
| 3,939,287 | 2/1976 | Orwig et al. | 422/32 X |
| 4,059,048 | 11/1977 | Dickson | 422/32 X |
| 4,532,115 | 7/1985 | Nishino et al. | 423/210 |
| 4,578,256 | 3/1986 | Nishino et al. | 423/210 |
| 4,579,714 | 4/1986 | Gunn | 422/29 X |
| 4,651,463 | 3/1987 | Friemel | 422/32 X |
| 4,756,117 | 7/1988 | Friemel | 422/305 |

OTHER PUBLICATIONS

J. W. Mellor, "A Comprehensive Treatise of Inorganic and Theoretical Chemistry, vol. VIII", Longmans, Green and Co., Mar. 1947.

*Primary Examiner*—Barry S. Richman
*Assistant Examiner*—Timothy M. McMahon
*Attorney, Agent, or Firm*—Millen & White

[57] ABSTRACT

This invention relates to a method of fumigating agricultural products in storage or transportation facilities for controlling pests by means of hydrogen phosphide which is then bound and/or decomposed to a substantial extent; according to the invention, a fumigating composition releasing hydrogen phosphide is placed in a manner known per se among products stored in conventional storage facilities, whereupon the stored products are covered with a flexible film, foil or sheet to isolate them from the surrounding storage space, and the hydrogen phosphide diffusing from the gas containing space above and among the stored products during or after fumigation is bound by adsorption, physical or chemical absorption and/or decomposed by chemical or physical means. The invention also relates to a specific solid catalyst suitable for the decomposition of hydrogen phosphide.

19 Claims, 1 Drawing Sheet

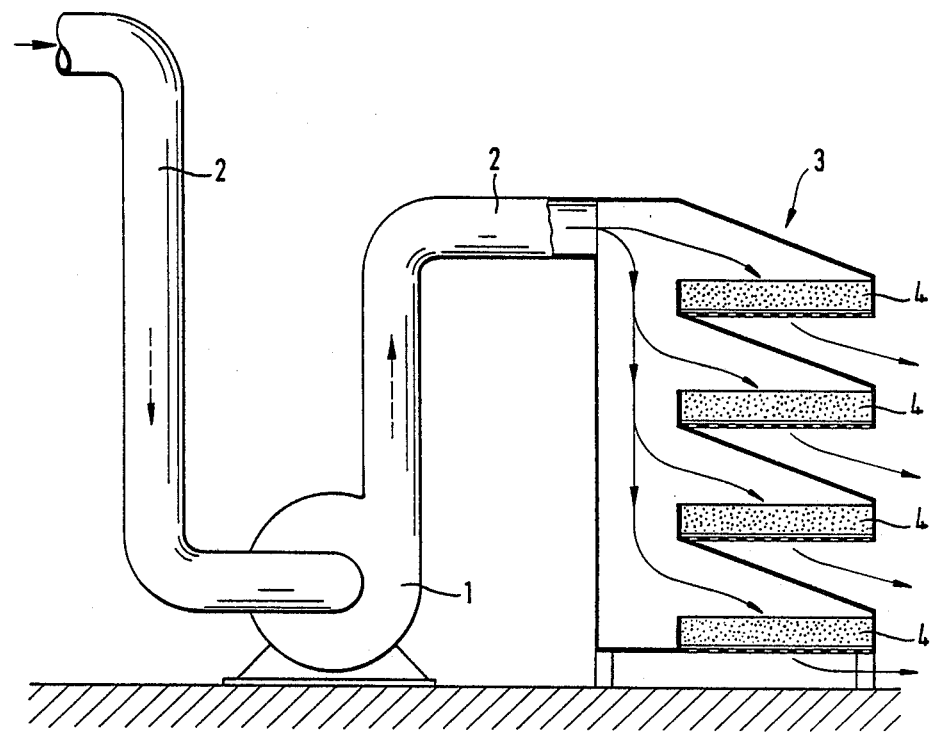

METHOD OF FUMIGATING AGRICULTURAL PRODUCTS USING HYDROGEN PHOSPHIDE

BACKGROUND OF THE INVENTION

The invention relates to a method of fumigating agricultural products in storage or transportation facilities for controlling pests with the aid of hydrogen phosphide which thereafter is bound and/or decomposed to a substantial extent.

For the last fifty years or so, hydrogen phosphide has proved to be a valuable fumigating agent for controlling pests in stored argricultural products. Compositions that release hydrogen phosphide have been made commercially available and have found worldwide acceptance since, to name only some of their advantages, they are highly efficient in controlling pests and easy to handle while the residues remaining after fumigation are harmless in ecological respects.

Fumigating compositions of the above type comprise as a major component some metal phosphide such as aluminum phosphide or magnesium phosphide, which hydrolyzes to give hydrogen phosphide under the influence of atmospheric humidity or moisture in the stored products. Such fumigating compositions may comprise additional components which either affect the developing rate of hydrogen phosphide in any desired manner, promote safety (especially when water seeps in), lower the phosphine concentration in the gas thus produced, improve the extent of gas development, or the like. Numerous phosphine-releasing compositions suitable for controlling pests are known, all of which may be used in the method of the invention. The particular form of the fumigating composition is not decisive either; suited are e.g. tablets, pellets, as well as powders packed in individual bags (sachets) or a series of interconnected bags.

Fumigation methods of the type described here are normally employed for controlling pests which attack agricultural products such as feedstuffs, grain, beans, peanuts and tobacco, in conventional storage facilities or transportation facilities such as railroad cars or the cargo holds of barges and ships.

The pests to be controlled in this manner may be rodents, but they usually are insects such as the corn weevil, Australian wheat weevil, saw-toothed grain beetle, grain borer, rice weevil and the like, as well as moths.

Up to now, fumigations were typically conducted in the following manner: Care had to be taken to establishing gas-tight conditions in the storage space containing the products to be fumigated so that phosphine could not escape into the atmosphere. The fumigating agent was then spread out and after the last person had left the respective facility, doors and other openings had to be sealed as well. After an appropriate exposure time during which the hydrogen phosphide could take effect on the parts in the stored products, the storage space had to be thoroughly ventilated to remove the hydrogen phosphide.

In contrast to residual products of the fumigating compositions which are quite harmless to the environment (and to humans) when fumigation is finished, hydrogen phosphide is highly toxic to mammals and humans. Morever, hydrogen phosphide gives off a strong, rather offensive odor reminescent of garlic, that is perceptible even at extremely low concentrations of about 0.02 pmm. Depending on the mode of application and the care taken in sealing off the storage space, hydrogen phosphide may escape into the atmosphere so that people living in the vicinity of the fumigation site will be unduly molested or even physically harmed. As the phosphine concentration cannot be determined by smelling, phosphine odors that suddenly occur (even if the concentration remains below the admissible level) may cause anxiety and sometimes nausea in particularly sensitive people. The same may happen when people approach the storage facility immediately after it has been ventilated in the conventional manner. Finally, in the interest of general protection from emissions of any type, one should always aim at releasing as little hydrogen phosphide as possible into the atmosphere.

SUMMARY OF THE INVENTION

Thus, it is an object of the present invention to provide a fumigation method for stored agricultural products, which avoids release of the employed hydrogen phosphide into the atmosphere so that people are neither molested nor harmed in any other way.

The present invention provides a method of fumigating agricultural products in storage or transportation facilities for controlling pests with the aid of hydrogen phosphide which is then bound and/or decomposed to a substantial extent, said method being characterized in that fumigating compositions releasing hydrogen phosphide are introduced in a manner known per se into agricultural products stored in conventional storage facilities, whereupon the stored products are covered with flexible films to isolate the products from the storage space, and the hydrogen phosphide escaping from the gas space above and among the stored products during or after fumigation is bound by adsorption, physical or chemical absorption and/or decomposed by chemical or physical means.

DETAILED DESCRIPTION

The phosphide containing fumigating compositions are introduced into the stored products in a conventional manner that is dependent only on the specific form in which these compositions are available commercially. Metal phosphide containing compositions, for instance, are frequently sold in the form of a powder or granular material packed in individual porous bags (sachets) or an assembly of interconnected porous bags. Such bags may be evenly distributed among the stored products by hand or by manually operated mechanical devices; individual bags are suitably tied to each other by strings threaded through loops at the ends of such bags. Some vertical practical devices for spreading out such fumigating compositions have already been described; these devices (known in the art as "bag blankets") comprise a plurality of connection bags in rolled-up or folded form which may then be easily unrolled or unfolded for use. All of the above modes of application are suited for the method according to the invention.

The subsequent covering of the stored products with a flexible foil or sheet is to be illustrated in the following by way of a specific embodiment of the invention, namely fumigation in a granary. Grain stock is usually stored in large containers with wooden walls. The method of the invention is, however, also applicable when grain is piled up on the floor of some other storage facility. Important is only that those sides of the grain pile where gas exchange is most likely to occur are covered by at least one flexible foil or sheet, e.g. of plastics. By practically isolating the stored products from the surrounding storage space in this manner, the gas exchange, including the diffusion of hydrogen phosphide into the storage space is obstructed to a greater or lesser extent.

Generally, two working principles are conceivable for the method of the invention: In the first case, gas exchange between the space directly above (and among) the stored products and the remaining storage space is impeded only to such an extent that during the fumigation period of several days or even several weeks substantially the entire phosphine diffuses from the gas space immediately above the stored products into the surrounding storage space where it is then bound and/or decomposed in the described manner. In the second case, the gas containing space above the stored products is sealed off so tightly that binding and/or decomposition of the hydrogen phosphide confined within that space is substantially effected only after fumigation is completed. The latter working principle is preferred to the method of the invention, as far as is practical.

However, any embodiment that constitutes a transition between the above described working principles is also conceivable for the method of the invention.

The desired extent to which gas exchange between the space abvoe the stored products and the surrounding storage space is to be impeded determines the measures required for covering the stored products and the selection of the material constituting the flexible foils or sheets. An essential criterion of the foil or sheet material is its inertness to the fumigating composition and stored products as well as adequate flexibility to ensure satisfactory covering of grain or other products to be fumigated. A large number of suitable plastic films or foils showing a variety of gas permeability values are available on the market. The extent of gas exchange between the gas space above the stored products and the surrounding storage space may thus be controlled to some degree by proper selection of the films from the variety of commercially available film materials.

When more than one panel of film is required for covering the stored products, the edges of such panel must overlap. To improve the sealing effect of the covering films, one may simply apply a suitable adhesive to the overlapping film portions. Useful adhesives are commercially available and require no description.

When the grain to be covered is heaped on the floor of some storage facility, the covering film should suitably extend over a sufficiently large section of the floor so as not to leave too much room for unhindered or unsatisfactorily hindered gas exchange. In this case, too, a temporary sealing between film and floor may be obtained by use of an adhesive. Adhesives may also be used for fastening the covering film to the side walls of storage tanks or the like.

Where the gas space above (and among) the stored products is isolated from the storage space by an impervious or practically impervious covering, means are suitably provided for exhausting the gas space above the stored products at the end of the fumigation period and for simultaneously binding or decomposing the hydrogen phosphide contained in the exhaust gas.

As mentioned before, any hydrogen phosphide diffusing from the gas space above the stored products is bound and/or decomposed in accordance with the invention. A large number of suitable methods of adsorption, chemical or physical absorption, and chemical or physical decomposition is known in the art so that a brief summary of such methods should suffice here.

A variety of materials having large surface areas may be used for adsorbing hydrogen phosphide. Illustrative of such materials are active carbon, molecular sieves, silica gel or aluminum hydroxide, the latter being preferably used in the form of pellets.

Useful in phosphine absorption are e.g. liquid media such as cyclohexanol, isopropanol, methanol and vegetable oils.

If desired, the loaded adsorbents or absorbents may subsequently be freed of phosphine by conventional procedures such as washing, heating, pressure reduction or the like, and may then be re-used. Treatment of the above type may of course be conducted in a closed system where the released phosphine no longer constitutes a molestation or a hazard.

Hydrogen phosphide may also be decomposed by chemical or physical means. Chemical decomposition is normally effected by oxidative treatment. A large number of oxidants are known for this purpose; mentioned as illustrative shall be only cuprous oxide, alkali and alkaline earth hypochlorites, particularly sodium and potassium hypochlorite, and potassium permanganate.

The use of known catalysts is frequently advantageous for the chemical decomposition of phosphine. Active carbon impregnated with specific transition metal compounds is particularly suited for the oxidative decomposition of phosphine. It is also known that active carbon thus impregnated may be subjected to thermal treatment before being used as a catalyst; the metal salt, e.g. copper sulphate or silver nitrate, used for impregnating the active carbon is thus converted into the corresponding oxide.

It has now been found that active carbon impregnated with alkali iodide provides excellent results in the oxidative decomposition of hydrogen phosphide. Preferred alkali iodides are potassium iodide and sodium iodide. The impregnated active carbon catalyst advantageously comprises from 0.1 to 4% by weight and preferably from 1 to 2% by weight of potassium iodide. Thus, active carbon impregnated with an alkali iodide is part of the invention.

In such chemical decomposition methods, oxidation of phosphine is effected by means of atmospheric oxygen and promoted by the above mentioned catalysts.

Hydrogen phosphide may also be decomposed by physical means, particularly by radiation such as ultraviolet radiation, or by thermal or electric treatment, provided the equipment required for such treatment is available at the fumigation site. In cases where the resulting decomposition products might lead to problems, it is a simple matter to further react the respective decomposition products in a manner known per se.

According to a specific embodiment of the method of the invention, the storage facility may be provided with air circulation means which permit circulation of the complete gas volume within a period of less than one hour, or from one to several hours, or from 10 to 24 hours.

Hydrogen phosphide diffusing from the gas space above the stored products need not necessarily be bound and/or decomposed within the respective storage facility. A gas purification system may also be disposed outside the storage facility if care is taken that air exhausted from the storage space is first passed through the gas purification unit and released into the atmosphere in a purified state.

The embodiment wherein the gas from the space above the stored products, which is then passed through gas purifying equipment for binding and/or decomposing any hydrogen phosphide contained therein, is exhausted only at the end of fumigation, is not the only possible approach, one may also continuously withdraw gas and pass it through the purifying equipment during the entire fumigation period, thus creating a pressure slightly below atmospheric in the space directly above the stored products or within the storage facility itself, respectively. In this manner, diffusion of phosphine containing gases is reduced or prevented at some other location.

It will be appreciated by a person skilled in the art that it is most desirable to carry out the process continuously, i.e. without interruption, until the hydrogen phosphide has been removed completely.

Gas purifying equipment suitable for use in the method of the invention may comprise a suction fan, proceded according to a particularly advantageous embodiment by a throttle, followed by connecting pipes and one or preferably several beds of a substance capable of binding and/or decomposing hydrogen phosphide, particularly a catalyst. In order to ensure a most effective use of said substance it should form as uniform a bed as possible. The flow rate of the gases to be purified is suitably kept between 0.1 and 0.5 m/s, e.g. at 0.32 m/s. When using a catalyst consisting of impregnated active carbon, the residence time of the gases within the catalyst bed may range from about 0.16 to 0.8 seconds and is e.g. 0.25 seconds. The thickness of the catalyst bed may suitably vary between 40 and 120 mm, particularly suited being a thickness of e.g. 80 mm. Under these conditions, the loss in flow pressure is 3.25 Pa/mm at 0.32 m/s.

BRIEF DESCRIPTION OF THE DRAWING

The drawing is a schematic representation of gas purifying equipment suitable for use in this invention.

The following example serves to illustrate the method of the invention.

EXAMPLE

The gas purifying equipment used in this example is schematically represented in the accompanying drawing. It comprises a suction fan (1), connecting pipes (2), catalyst (3) and beds (4) of active carbon. The invention is not limited to the number of catalyst beds shown in the drawing.

Impregnated active carbon is present in the form of solid bed layers supported on perforated trays (5 mm perforations), each of which is covered by a pad of polypropylene fleece material. Exhaust gas flows through these layers at a rate of 0.28 m/s; at a layer thickness of 80 mm, the residence time thus is 0.29 seconds. Suitable particular sizes of the active carbon are for example in the range of 2 to 4 mm.

The effective catalyst surface area may be selected at will by stacking a desired number of trays. In a particular case two stacks of six trays each were used plus one initial and one terminal piece. Each tray contained 30 kg of active carbon over an area of 1 sq.m.

The active carbon used contained 2% of potassium iodide. Gas thus purified showed no detectable traces of $PH_3$; according to present measuring standards, this means that the $PH_3$ content of the purified gas was always below 0.5 parts per billion even if the crude gas showed concentrations of several hundred parts per million.

The oxidation product ($P_2O_5$) is deposited on the active carbon and shows hygroscopic behavior. Extremely wet gases (moisture content 80 to 90%) cause the formation of highly viscous phosphoric acid which, when present in large amounts, may clog up the pores of the active carbon. Catalyst loading is thus limited to 65 grams of $PH_3$ per 100 grams of active carbon. The dimensions of the catalyst beds were determined on the basis of the above load, a 100% reserve being included.

For the above reasons, the catalyst must be replaced at certain intervals or regenerated by e.g. washing to remove phosphoric acid deposited thereon.

What is claimed is:

1. A method for preventing the release into the atmosphere of hydrogen phosphide during or after the fumigation therewith of an agricultural product stored in a bulk storage or transportation facility which is only partially filled therewith and from which hydrogen phosphide can escape during or after the fumigation, which comprises the steps of:
    (a) covering the exposed outer surface of the stored product with a flexible sheet material which is at least substantially gas impervious, in a manner which isolates the stored product from the surrounding unfilled storage space in the facility and at least hinders gas exchange between the filled portion of the storage space of the facility beneath the flexible material and the filled space above the flexible material;
    (b) introducing a fumigating amount of hydrogen phosphide into the thus-covered stored product;
    (c) actively withdrawing and collecting air from the unfilled storage space above the covered product in an amount effective to prevent hydrogen phosphide from escaping into the atmosphere from the facility; and
    (d) removing any hydrogen phosphide in the withdrawn air therefrom before discharging that air into the atmosphere.

2. Method according to claim 1, wherein, the step of removal of hydrogen phosphide comprises adsorption of hydrogen phosphide by adsorptive binding to a member of the group consisting of active carbon, molecular sieves, silica gel and aluminum hydroxide.

3. Method according to claim 1, wherein the step of removal of hydrogen phosphide comprises absorption of hydrogen phosphide by a member of the group consisting of cyclohexanol, isopropanol, methanol and a vegatable oil.

4. Method according to claim 1, wherein the step of removal of the hydrogen phosphide comprise decomposition thereof by physical means.

5. Method according to claim 1, wherein air circulation means is provided in the storage or transportation facility which provides circulation of air therein at a rate of a complete gas volume in up to 24 hours.

6. Method according to claim 1, wherein the emitted hydrogen phosphide is removed in gas purifying equipment disposed outside of the storage or transportation facility by passing air from the storage or transportation facility through said gas purifying equipment and subsequently releasing the purified air into the atmosphere.

7. Method according to claim 1, wherein removal of hydrogen phosphide is promoted by local reduction of the partial pressure.

8. Method according to claim 1, wherein the stored products are covered by applying overlapping panels of sheet thereover and sealing the overlapping portions of the panels to gas by applying an adhesive thereto.

9. Method according to claim 1, wherein only small quantities of hydrogen phosphide are emitted during fumigation, wherein the gas containing space above the stored products is exhausted after fumigation, and wherein the exhausted gas is then passed through gas purifying equipment.

10. Method according to claim 1, wherein the stored products are covered by applying overlapping panels of sheet thereover and sealing the overlapping portions of the panels to gas by applying an adhesive thereto; wherein air circulation means is provided in the storage or transportation facility which provides circulation of air therein at a rate of a complete gas volume in up to 24 hours; wherein emitted hydrogen phosphide is removed in gas purifying equipment disposed outside of the storage facility by passing air from the storage or transportation facility through said gas purifying equipment and subsequently releasing the purified air into the atmosphere; and wherein removal of hydrogen phoshide is promoted by local reduction of the partial pressure.

11. Method according to claim 1, wherein the step of removal of the hydrogen phosphide comprises passing the withdrawn air through a gas permeable filter impregnated with a catalyst which catalyzes the oxidation of the hydrogen phosphide by the oxygen in the stream of air.

12. Method according to claim 1, wherein the step of removal of the hydrogen phosphide comprises decomposition there with the aid of a solid catalyst.

13. Method according to claim 12, wherein the solid catalyst is activated carbon which has been impregnated with a member of the group consisting of an alkali iodide, copper sulphate, iron sulphate, an alkali chromate and an alkali dichromate.

14. Method according to claim 1, wherein the step of removal of the hydrogen phosphide comprises decomposition thereof with the storage or transportation facility by oxidation.

15. Method according to claim 14, wherein oxidation is effected with a member of the group consisting of cuprous oxide, silver nitrate, alkali or alkaline earth hypochlorite, and potassium permanganate.

16. Method according to claim 14, wherein the oxidation is conducted with heating.

17. Method according to claim 1, wherein the step of removal of the hydrogen phosphide comprises decomposition of the emitted hydrogen phosphide which decomposition is catalyzed with a solid catalyst which comprises carbon impregnated with an alkyl iodide.

18. Method according to claim 17 wherein the catalyst comprises potassium iodide in an amount of from 0.1 to 4% by weight, based on the total weight of the catalyst.

19. Method according to claim 18, wherein the potassium iodide is present in an amount of from 1 to 2% by weight.

* * * * *